US012104180B2

(12) United States Patent
Li et al.

(10) Patent No.: US 12,104,180 B2
(45) Date of Patent: Oct. 1, 2024

(54) ENZYME WITH ACYL TRANSFER FUNCTION AND APPLICATION THEREOF

(71) Applicant: OCEAN UNIVERSITY OF CHINA, Shandong (CN)

(72) Inventors: Wenli Li, Shandong (CN); Fei Xiao, Shandong (CN); Yang Liu, Shandong (CN); Huayue Li, Shandong (CN)

(73) Assignee: OCEAN UNIVERSITY OF CHINA, Shandong (CN)

( * ) Notice: Subject to any disclaimer, the term of this patent is extended or adjusted under 35 U.S.C. 154(b) by 588 days.

(21) Appl. No.: 17/432,099

(22) PCT Filed: Dec. 7, 2020

(86) PCT No.: PCT/CN2020/134158
§ 371 (c)(1),
(2) Date: Aug. 19, 2021

(87) PCT Pub. No.: WO2021/159828
PCT Pub. Date: Aug. 19, 2021

(65) Prior Publication Data
US 2022/0145271 A1 May 12, 2022

(30) Foreign Application Priority Data
Feb. 10, 2020 (CN) .......................... 202010083819.4

(51) Int. Cl.
*C12P 17/08* (2006.01)
*C12N 9/10* (2006.01)

(52) U.S. Cl.
CPC ............ *C12N 9/1025* (2013.01); *C12P 17/08* (2013.01)

(58) Field of Classification Search
CPC ............................... C12N 9/1025; C12P 17/08
See application file for complete search history.

(56) References Cited

PUBLICATIONS

Wang et al., Draft genome sequence of a plant growth-promoting bacteria: Bacillus amyloliquefaciens A3. Submitted Jan. 2014 to the EMBL/GenBank/DDBJ databases, Strain EBL11 ECO:0000313, EMBL:EYB35116.1 (Year: 2014).*
Xiao et al., Structural Basis of Specificity for Carboxyl-Terminated Acyl Donors in a Bacterial Acyltransferase 2020, Journal of the American Chemical Society, 142: 16031-16038 (Year: 2020).*

(Continued)

*Primary Examiner* — James H Alstrum-Acevedo
*Assistant Examiner* — Saleha Kuzniewski

(57) ABSTRACT

An enzyme with an acyl transfer function has an amino acid sequence identical to a SEQ ID NO:1, which is capable of acylation modification for macrolactins, filipins macrolides, chloramphenicol, and glycosylated piericidin A. An application of an acyltransferase of the present invention is to bind an acyl group of an acyl donor to macrolide compounds, chloramphenicol and glycosylated piericidins. The enzyme with the acyl transfer function can improve pharmacological activity of the macrolide compounds through acylation reaction of macrolactins, thereby improving bioavailability, enhancing efficacy, and reducing toxic as well as side effects, which provides a new strategy for the drug development of macrolide compounds.

3 Claims, 5 Drawing Sheets

Specification includes a Sequence Listing.

(56) References Cited

PUBLICATIONS

Liu et al. Genome-wide identification and characterization of macrolide glycosyltransferases from amarine-derived Bacillus strain and their phylogenetic distribution, 2016, Environmental Microbiology, 18(12): 4770-4781). (Year: 2016).*

Wang et al., Draft genome sequence of a plant growth-promoting bacteria: Bacillus amyloliquefaciens A3. Submitted Jan. 2014 to the EMBL/GenBank/DDBJ databases, Strain EBL11 ECO:0000313, EMBL:EYB35116.1 (Year: 2014) (Year: 2014).*

* cited by examiner

SEQUENCE LISTING

```
<160> NUMBER OF SEQ ID NOS: 14

<210> SEQ ID NO 1
<211> LENGTH: 363
<212> TYPE: PRT
<213> ORGANISM: Artificial Sequence
<220> FEATURE:
<223> OTHER INFORMATION: bmmI acyltransferase protease sequence

<400> SEQUENCE: 1

Met Lys Gln Thr Ile Ser Asn Pro Ala Phe Asp Met Lys Gln Ile Asn
1               5                   10                  15

Ala Leu Asn Gly His Tyr Gln Thr Met Ile Asp Asn Gly Asp Leu Gln
            20                  25                  30

Cys Ala Ser Tyr Met Met Ser Arg Gly Gly Glu Val Phe Ala Ala Glu
        35                  40                  45

Ser Leu Gly Glu Phe Thr Gly Gly Gln Lys Glu Lys Gln Thr Phe Gln
    50                  55                  60

Leu Asp Thr Ile Arg Glu Ile Gly Ser Leu Thr Lys Val Phe Thr Ala
65                  70                  75                  80

Val Ala Val Met Gln Leu Val Glu Lys Gly Leu Leu Asp Leu Lys Met
                85                  90                  95

Pro Val Lys Leu Ile Leu Pro Ala Phe Asp Lys Pro Gly Phe Gly Glu
            100                 105                 110

Ile Lys Ile Leu His Leu Leu Thr His Thr Ala Gly Leu Ser Phe Glu
        115                 120                 125

Leu Asp Ile Gln Lys Ala Glu Gly Ile Asp Leu Thr Asn Glu Glu Glu
    130                 135                 140

Trp Ile Asn Tyr Leu Val Ser Thr Pro Leu Glu Tyr Gly Val Asp Glu
145                 150                 155                 160
```

```
Ala Trp Asn Tyr Ser Arg Thr Gly Phe Val Ile Gly Ile Ile Ile
            165                 170                 175

Ser Lys Val Thr Gly Val Ser Tyr Glu Gln Tyr Val Thr Lys His Ile
            180                 185                 190

Ile Glu Ala Leu Gly Leu Glu Arg Thr Tyr Phe Tyr Val Pro Asp Thr
            195                 200                 205

Leu Lys Glu Glu Val Cys Val Ile Ser Glu His Glu Cys Val Gln Leu
210                 215                 220

Glu Lys Ser His His Pro Tyr Phe Pro Asn Lys Ala Thr Ser Gly Leu
225                 230                 235                 240

Tyr Ser Ser Leu Arg Asp Ile Trp Lys Leu Ala Glu Met Phe Arg Asn
            245                 250                 255

Lys Gly Arg Leu Lys Asp Lys Lys Leu Leu Gly Arg Lys Thr Val Glu
            260                 265                 270

Ala Met Leu Arg Asn Gln Ile Lys Pro Gly Leu Pro Phe Tyr Phe Phe
            275                 280                 285

Gly Ala Pro Arg Glu Glu Gly Gly Phe Gly Leu Gly Ile Asn Leu Trp
        290                 295                 300

Pro Ala Gly Asp His Tyr Phe Met Thr Glu Gly Thr Phe Ser His Leu
305                 310                 315                 320

Gly Met Gly Trp Cys Gly Met Phe Ser Asp Pro Ala Glu Asp Phe Thr
                325                 330                 335

Tyr Val Phe Phe Thr Pro Ile Ser Glu Phe His Pro His Ala Val Leu
            340                 345                 350

Thr Pro Leu Asn Ile Val Trp Ala Gly Ile Glu
        355                 360

<210> SEQ ID NO 2
<211> LENGTH: 1092
<212> TYPE: DNA
<213> ORGANISM: Artificial Sequence
<220> FEATURE:
<223> OTHER INFORMATION: bmmI acyltransferase nucleotide sequence

<400> SEQUENCE: 2
atgaaacaaa caataagcaa tccggcattt gatatgaaac aaattaacgc tcttaacggc      60
cattatcaga cgatgataga caatggagat ctgcaatgtg cgagttatat gatgtcaaga     120
ggaggtgagg tttttgcagc tgagtcgtta ggggaattta ccggcggaca aaagaaaag      180 caaacatttc agcttgatac aatcagagaa atcggttctt tgacaaaagt gtttaccgct     240
gtagccgtca tgcagctcgt cgaaaaaggt ttgctcgatc tgaaaatgcc ggtcaagctc     300
attttgccag cgtttgataa accgggtttc ggagaaatta aattttgca ccttttgact      360 catacggcgg gattaagttt tgagctggat attcaaaagg ctgaaggcat tgacttaacg     420
aatgaggaag aatggataaa ctatctggtc agtacgcctt ggagtacgg agtggatgaa      480 gcatggaact attccagaac cggctttgtt atacttggca tcattattttc aaaagtaaca     540 ggcgtatcct acgaacagta tgtaacaaag catattattg aagcgctcgg attagaaaga     600 acgtatttt atgtgcctga tactttaaaa gaagaagttt gtgtgatcag tgagcacgag      660
tgcgtacagc tggaaaaaag tcatcacccg tatttccga ataaagcgac aagcggtctg      720
tactcttcgt tgcgagatat ttggaagtta gctgaaatgt ttagaaataa aggcagattg     780
aaagataaga agctgcttgg aagaaaaaca gtcgaagcga tgctgagaaa tcaaataaag     840
cccggtcttc cttttactt cttcggagcg cccagagagg aaggcggctt tggtttaggc     900
```

```
attaatttgt ggccggccgg tgaccattat ttcatgacag aaggcacctt ctcacatctt    960
ggaatgggtt ggtgcggcat gttttctgat ccagccgaag attttacgta tgtatttttc   1020
actccgattt ccgagtttca tcctcatgcc gtgctgacgc cgctgaatat cgtgtgggcg   1080
ggtattgaat aa                                                       1092
```

```
<210> SEQ ID NO 3
<211> LENGTH: 363
<212> TYPE: PRT
<213> ORGANISM: Artificial Sequence
<220> FEATURE:
<223> OTHER INFORMATION: mutant protein R166A amino acid sequence

<400> SEQUENCE: 3

Met Lys Gln Thr Ile Ser Asn Pro Ala Phe Asp Met Lys Gln Ile Asn
1               5                   10                  15

Ala Leu Asn Gly His Tyr Gln Thr Met Ile Asp Asn Gly Asp Leu Gln
            20                  25                  30

Cys Ala Ser Tyr Met Met Ser Arg Gly Gly Glu Val Phe Ala Ala Glu
        35                  40                  45

Ser Leu Gly Glu Phe Thr Gly Gly Gln Lys Glu Lys Gln Thr Phe Gln
    50                  55                  60

Leu Asp Thr Ile Arg Glu Ile Gly Ser Leu Thr Lys Val Phe Thr Ala
65                  70                  75                  80

Val Ala Val Met Gln Leu Val Glu Lys Gly Leu Leu Asp Leu Lys Met
                85                  90                  95

Pro Val Lys Leu Ile Leu Pro Ala Phe Asp Lys Pro Gly Phe Gly Glu
            100                 105                 110

Ile Lys Ile Leu His Leu Leu Thr His Thr Ala Gly Leu Ser Phe Glu
        115                 120                 125

Leu Asp Ile Gln Lys Ala Glu Gly Ile Asp Leu Thr Asn Glu Glu Glu
    130                 135                 140

Trp Ile Asn Tyr Leu Val Ser Thr Pro Leu Glu Tyr Gly Val Asp Glu
145                 150                 155                 160

Ala Trp Asn Tyr Ser Ala Thr Gly Phe Val Ile Leu Gly Ile Ile Ile
                165                 170                 175

Ser Lys Val Thr Gly Val Ser Tyr Glu Gln Tyr Val Thr Lys His Ile
            180                 185                 190

Ile Glu Ala Leu Gly Leu Glu Arg Thr Tyr Phe Tyr Val Pro Asp Thr
        195                 200                 205

Leu Lys Glu Glu Val Cys Val Ile Ser Glu His Glu Cys Val Gln Leu
    210                 215                 220

Glu Lys Ser His His Pro Tyr Phe Pro Asn Lys Ala Thr Ser Gly Leu
225                 230                 235                 240

Tyr Ser Ser Leu Arg Asp Ile Trp Lys Leu Ala Glu Met Phe Arg Asn
                245                 250                 255

Lys Gly Arg Leu Lys Asp Lys Lys Leu Leu Gly Arg Lys Thr Val Glu
            260                 265                 270

Ala Met Leu Arg Asn Gln Ile Lys Pro Gly Leu Pro Phe Tyr Phe Phe
        275                 280                 285

Gly Ala Pro Arg Glu Glu Gly Gly Phe Gly Leu Gly Ile Asn Leu Trp
    290                 295                 300

Pro Ala Gly Asp His Tyr Phe Met Thr Glu Gly Thr Phe Ser His Leu
305                 310                 315                 320
```

```
Gly Met Gly Trp Cys Gly Met Phe Ser Asp Pro Ala Glu Asp Phe Thr
            325                 330                 335

Tyr Val Phe Phe Thr Pro Ile Ser Glu Phe His Pro His Ala Val Leu
        340                 345                 350

Thr Pro Leu Asn Ile Val Trp Ala Gly Ile Glu
        355                 360

<210> SEQ ID NO 4
<211> LENGTH: 1092
<212> TYPE: DNA
<213> ORGANISM: Artificial Sequence
<220> FEATURE:
<223> OTHER INFORMATION: mutant protein R166A nucleotide sequence

<400> SEQUENCE: 4
atgaaacaaa caataagcaa tccggcattt gatatgaaac aaattaacgc tcttaacggc      60
cattatcaga cgatgataga caatggagat ctgcaatgtg cgagttatat gatgtcaaga     120
ggaggtgagg tttttgcagc tgagtcgtta ggggaattta ccggcggaca aaaagaaaag     180
caaacatttc agcttgatac aatcagagaa atcggttctt tgacaaaagt gtttaccgct     240
gtagccgtca tgcagctcgt cgaaaaaggt ttgctcgatc tgaaaatgcc ggtcaagctc     300
attttgccag cgtttgataa accgggtttc ggagaaatta aaattttgca ccttttgact     360
catacggcgg gattaagttt tgagctggat attcaaaagg ctgaaggcat tgacttaacg     420
aatgaggaag aatggataaa ctatctggtc agtacgcctt tggagtacgg agtggatgaa     480
gcatggaact attccgcaac cggctttgtt atacttggca tcattatttc aaaagtaaca     540
ggcgtatcct acgaacagta tgtaacaaag catattattg aagcgctcgg attagaaaga     600
acgtattttt atgtgcctga tactttaaaa gaagaagttt gtgtgatcag tgagcacgag     660
tgcgtacagc tggaaaaaag tcatcacccg tattttccga ataaagcgac aagcggtctg     720
tactcttcgt tgcgagatat ttggaagtta gctgaaatgt ttagaaataa aggcagattg     780
aaagataaga agctgcttgg aagaaaaaca gtcgaagcga tgctgagaaa tcaaataaag     840
cccggtcttc cttttactt cttcggagcg cccagagagg aaggcggctt tggtttaggc     900
attaatttgt ggccggccgg tgaccattat ttcatgacga aaggcacctt ctcacatctt     960
ggaatgggtt ggtgcggcat gttttctgat ccagccgaag attttacgta tgtattttc     1020
actccgattt ccgagtttca tcctcatgcc gtgctgacgc cgctgaatat cgtgtgggcg     1080
ggtattgaat aa                                                         1092

<210> SEQ ID NO 5
<211> LENGTH: 363
<212> TYPE: PRT
<213> ORGANISM: Artificial Sequence
<220> FEATURE:
<223> OTHER INFORMATION: mutant protein R166G amino acid sequence

<400> SEQUENCE: 5

Met Lys Gln Thr Ile Ser Asn Pro Ala Phe Asp Met Lys Gln Ile Asn
  1               5                  10                  15

Ala Leu Asn Gly His Tyr Gln Thr Met Ile Asp Asn Gly Asp Leu Gln
             20                  25                  30

Cys Ala Ser Tyr Met Met Ser Arg Gly Gly Glu Val Phe Ala Ala Glu
         35                  40                  45

Ser Leu Gly Glu Phe Thr Gly Gly Gln Lys Glu Lys Gln Thr Phe Gln
     50                  55                  60
```

```
Leu Asp Thr Ile Arg Glu Ile Gly Ser Leu Thr Lys Val Phe Thr Ala
 65                  70                  75                  80

Val Ala Val Met Gln Leu Val Glu Lys Gly Leu Leu Asp Leu Lys Met
                 85                  90                  95

Pro Val Lys Leu Ile Leu Pro Ala Phe Asp Lys Pro Gly Phe Gly Glu
            100                 105                 110

Ile Lys Ile Leu His Leu Leu Thr His Thr Ala Gly Leu Ser Phe Glu
            115                 120                 125

Leu Asp Ile Gln Lys Ala Glu Gly Ile Asp Leu Thr Asn Glu Glu
130                 135                 140

Trp Ile Asn Tyr Leu Val Ser Thr Pro Leu Glu Tyr Gly Val Asp Glu
145                 150                 155                 160

Ala Trp Asn Tyr Ser Gly Thr Gly Phe Val Ile Leu Gly Ile Ile Ile
                165                 170                 175

Ser Lys Val Thr Gly Val Ser Tyr Glu Gln Tyr Val Thr Lys His Ile
                180                 185                 190

Ile Glu Ala Leu Gly Leu Glu Arg Thr Tyr Phe Tyr Val Pro Asp Thr
            195                 200                 205

Leu Lys Glu Glu Val Cys Val Ile Ser Glu His Glu Cys Val Gln Leu
210                 215                 220

Glu Lys Ser His His Pro Tyr Phe Pro Asn Lys Ala Thr Ser Gly Leu
225                 230                 235                 240

Tyr Ser Ser Leu Arg Asp Ile Trp Lys Leu Ala Glu Met Phe Arg Asn
                245                 250                 255

Lys Gly Arg Leu Lys Asp Lys Lys Leu Leu Gly Arg Lys Thr Val Glu
            260                 265                 270

Ala Met Leu Arg Asn Gln Ile Lys Pro Gly Leu Pro Phe Tyr Phe Phe
            275                 280                 285

Gly Ala Pro Arg Glu Glu Gly Gly Phe Gly Leu Gly Ile Asn Leu Trp
            290                 295                 300

Pro Ala Gly Asp His Tyr Phe Met Thr Glu Gly Thr Phe Ser His Leu
305                 310                 315                 320

Gly Met Gly Trp Cys Gly Met Phe Ser Asp Pro Ala Glu Asp Phe Thr
                325                 330                 335

Tyr Val Phe Phe Thr Pro Ile Ser Glu Phe His Pro His Ala Val Leu
                340                 345                 350

Thr Pro Leu Asn Ile Val Trp Ala Gly Ile Glu
            355                 360
```

<210> SEQ ID NO 6
<211> LENGTH: 1092
<212> TYPE: DNA
<213> ORGANISM: Artificial Sequence
<220> FEATURE:
<223> OTHER INFORMATION: mutant protein R166G nucleotide sequence

<400> SEQUENCE: 6

```
atgaaacaaa caataagcaa tccggcattt gatatgaaac aaattaacgc tcttaacggc      60
cattatcaga cgatgataga caatggagat ctgcaatgtg cgagttatat gatgtcaaga     120
ggaggtgagg ttttgcagc tgagtcgtta ggggaattta ccgcggaca aaagaaaag      180 caaacattc agcttgatac aatcagagaa atcggttctt tgacaaaagt gtttaccgct     240
gtagccgtca tgcagctcgt cgaaaaaggt ttgctcgatc tgaaaatgcc ggtcaagctc     300
attttgccag cgtttgataa accgggttc ggagaaatta aaattttgca ccttttgact     360
```

-continued

```
catacggcgg gattaagttt tgagctggat attcaaaagg ctgaaggcat tgacttaacg    420
aatgaggaag aatggataaa ctatctggtc agtacgcctt tggagtacgg agtggatgaa    480
gcatggaact attccggtac cggctttgtt atacttggca tcattatttc aaaagtaaca    540
ggcgtatcct acgaacagta tgtaacaaag catattattg aagcgctcgg attagaaaga    600
acgtattttt atgtgcctga tactttaaaa gaagaagttt gtgtgatcag tgagcacgag    660
tgcgtacagc tggaaaaaag tcatcacccg tatttccga ataaagcgac aagcggtctg     720
tactcttcgt tgcgagatat ttggaagtta gctgaaatgt ttagaaataa aggcagattg    780
aaagataaga agctgcttgg aagaaaaaca gtcgaagcga tgctgagaaa tcaaataaag    840
cccggtcttc cttttactt cttcggagcg cccagagagg aaggcggctt tggtttaggc     900
attaatttgt ggccggccgg tgaccattat ttcatgacag aaggcacctt ctcacatctt    960
ggaatgggtt ggtgcggcat gttttctgat ccagccgaag attttacgta tgtattttc   1020 actccgattt ccgagtttca tcctcatgcc gtgctgacgc cgctgaatat cgtgtgggcg   1080
ggtattgaat aa                                                      1092
```

<210> SEQ ID NO 7
<211> LENGTH: 363
<212> TYPE: PRT
<213> ORGANISM: Artificial Sequence
<220> FEATURE:
<223> OTHER INFORMATION: mutant protein R166K amino acid sequence

<400> SEQUENCE: 7

```
Met Lys Gln Thr Ile Ser Asn Pro Ala Phe Asp Met Lys Gln Ile Asn
1               5                   10                  15

Ala Leu Asn Gly His Tyr Gln Thr Met Ile Asp Asn Gly Asp Leu Gln
            20                  25                  30

Cys Ala Ser Tyr Met Met Ser Arg Gly Gly Glu Val Phe Ala Ala Glu
        35                  40                  45

Ser Leu Gly Glu Phe Thr Gly Gly Gln Lys Glu Lys Gln Thr Phe Gln
    50                  55                  60

Leu Asp Thr Ile Arg Glu Ile Gly Ser Leu Thr Lys Val Phe Thr Ala
65                  70                  75                  80

Val Ala Val Met Gln Leu Val Glu Lys Gly Leu Leu Asp Leu Lys Met
                85                  90                  95

Pro Val Lys Leu Ile Leu Pro Ala Phe Asp Lys Pro Gly Phe Gly Glu
            100                 105                 110

Ile Lys Ile Leu His Leu Thr His Thr Ala Gly Leu Ser Phe Glu
        115                 120                 125

Leu Asp Ile Gln Lys Ala Glu Gly Ile Asp Leu Thr Asn Glu Glu Glu
    130                 135                 140

Trp Ile Asn Tyr Leu Val Ser Thr Pro Leu Glu Tyr Gly Val Asp Glu
145                 150                 155                 160

Ala Trp Asn Tyr Ser Lys Thr Gly Phe Val Ile Leu Gly Ile Ile Ile
                165                 170                 175

Ser Lys Val Thr Gly Val Ser Tyr Glu Gln Tyr Val Thr Lys His Ile
            180                 185                 190

Ile Glu Ala Leu Gly Leu Glu Arg Thr Tyr Phe Tyr Val Pro Asp Thr
        195                 200                 205

Leu Lys Glu Glu Val Cys Val Ile Ser Glu His Glu Cys Val Gln Leu
    210                 215                 220

Glu Lys Ser His His Pro Tyr Phe Pro Asn Lys Ala Thr Ser Gly Leu
```

```
            225                 230                 235                 240
Tyr Ser Ser Leu Arg Asp Ile Trp Lys Leu Ala Glu Met Phe Arg Asn
                    245                 250                 255

Lys Gly Arg Leu Lys Asp Lys Lys Leu Leu Gly Arg Lys Thr Val Glu
                260                 265                 270

Ala Met Leu Arg Asn Gln Ile Lys Pro Gly Leu Pro Phe Tyr Phe Phe
            275                 280                 285

Gly Ala Pro Arg Glu Glu Gly Phe Gly Leu Gly Ile Asn Leu Trp
        290                 295                 300

Pro Ala Gly Asp His Tyr Phe Met Thr Glu Gly Thr Phe Ser His Leu
305                 310                 315                 320

Gly Met Gly Trp Cys Gly Met Phe Ser Asp Pro Ala Glu Asp Phe Thr
                    325                 330                 335

Tyr Val Phe Phe Thr Pro Ile Ser Glu Phe His Pro His Ala Val Leu
                340                 345                 350

Thr Pro Leu Asn Ile Val Trp Ala Gly Ile Glu
                355                 360
```

<210> SEQ ID NO 8
<211> LENGTH: 1092
<212> TYPE: DNA
<213> ORGANISM: Artificial Sequence
<220> FEATURE:
<223> OTHER INFORMATION: mutant protein R166K nucleotide sequence

<400> SEQUENCE: 8

```
atgaaacaaa caataagcaa tccggcattt gatatgaaac aaattaacgc tcttaacggc    60
cattatcaga cgatgataga caatggagat ctgcaatgtg cgagttatat gatgtcaaga   120
ggaggtgagg tttttgcagc tgagtcgtta ggggaattta ccgcggaca aaaagaaaag   180
caaacatttc agcttgatac aatcagagaa atcggttctt tgacaaaagt gtttaccgct   240
gtagccgtca tgcagctcgt cgaaaaaggt ttgctcgatc tgaaaatgcc ggtcaagctc   300
attttgccag cgtttgataa accgggtttc ggagaaatta aaattttgca cctttttgact   360
catacggcgg gattaagttt tgagctggat attcaaaagg ctgaaggcat tgacttaacg   420
aatgaggaag aatggataaa ctatctggtc agtacgcctt ggagtacgg agtggatgaa   480
gcatggaact attccaaaac cggctttgtt tacttggca tcattatttc aaaagtaaca   540
ggcgtatcct acgaacagta tgtaacaaag catattattg aagcgctcgg attagaaaga   600
acgtattttt atgtgcctga tactttaaaa gaagaagttt gtgtgatcag tgagcacgag   660
tgcgtacagc tggaaaaaag tcatcacccg tattttccga taaagcgac aagcggtctg   720
tactcttcgt tgcgagatat ttggaagtta gctgaaatgt ttagaaataa aggcagattg   780
aaagataaga agctgcttgg aagaaaaaca gtcgaagcga tgctgagaaa tcaaataaag   840
cccggtcttc ctttttactt cttcggagcg cccagagagg aaggcggctt tggtttaggc   900
attaatttgt ggccggccgg tgaccattat ttcatgacag aaggcacctt ctcacatctt   960
ggaatgggtt ggtgcggcat gttttctgat ccagccgaag attttacgta tgtatttttc  1020
actccgattt ccgagtttca tcctcatgcc gtgctgacgc cgctgaatat cgtgtgggcg  1080
ggtattgaat aa                                                       1092
```

<210> SEQ ID NO 9
<211> LENGTH: 363
<212> TYPE: PRT
<213> ORGANISM: Artificial Sequence
<220> FEATURE:
<223> OTHER INFORMATION: mutant protein R166Q amino acid sequence

<400> SEQUENCE: 9

Met Lys Gln Thr Ile Ser Asn Pro Ala Phe Asp Met Lys Gln Ile Asn
1               5                   10                  15

Ala Leu Asn Gly His Tyr Gln Thr Met Ile Asp Asn Gly Asp Leu Gln
            20                  25                  30

Cys Ala Ser Tyr Met Met Ser Arg Gly Gly Glu Val Phe Ala Ala Glu
        35                  40                  45

Ser Leu Gly Glu Phe Thr Gly Gly Gln Lys Glu Lys Gln Thr Phe Gln
    50                  55                  60

Leu Asp Thr Ile Arg Glu Ile Gly Ser Leu Thr Lys Val Phe Thr Ala
65                  70                  75                  80

Val Ala Val Met Gln Leu Val Glu Lys Gly Leu Leu Asp Leu Lys Met
                85                  90                  95

Pro Val Lys Leu Ile Leu Pro Ala Phe Asp Lys Pro Gly Phe Gly Glu
            100                 105                 110

Ile Lys Ile Leu His Leu Leu Thr His Thr Ala Gly Leu Ser Phe Glu
        115                 120                 125

Leu Asp Ile Gln Lys Ala Glu Gly Ile Asp Leu Thr Asn Glu Glu Glu
    130                 135                 140

Trp Ile Asn Tyr Leu Val Ser Thr Pro Leu Glu Tyr Gly Val Asp Glu
145                 150                 155                 160

Ala Trp Asn Tyr Ser Gln Thr Gly Phe Val Ile Leu Gly Ile Ile Ile
                165                 170                 175

Ser Lys Val Thr Gly Val Ser Tyr Glu Gln Tyr Val Thr Lys His Ile
            180                 185                 190

Ile Glu Ala Leu Gly Leu Glu Arg Thr Tyr Phe Tyr Val Pro Asp Thr
        195                 200                 205

Leu Lys Glu Glu Val Cys Val Ile Ser Glu His Glu Cys Val Gln Leu
    210                 215                 220

Glu Lys Ser His His Pro Tyr Phe Pro Asn Lys Ala Thr Ser Gly Leu
225                 230                 235                 240

Tyr Ser Ser Leu Arg Asp Ile Trp Lys Leu Ala Glu Met Phe Arg Asn
                245                 250                 255

Lys Gly Arg Leu Lys Asp Lys Lys Leu Leu Gly Arg Lys Thr Val Glu
            260                 265                 270

Ala Met Leu Arg Asn Gln Ile Lys Pro Gly Leu Pro Phe Tyr Phe Phe
        275                 280                 285

Gly Ala Pro Arg Glu Glu Gly Gly Phe Gly Leu Gly Ile Asn Leu Trp
    290                 295                 300

Pro Ala Gly Asp His Tyr Phe Met Thr Glu Gly Thr Phe Ser His Leu
305                 310                 315                 320

Gly Met Gly Trp Cys Gly Met Phe Ser Asp Pro Ala Glu Asp Phe Thr
                325                 330                 335

Tyr Val Phe Phe Thr Pro Ile Ser Glu Phe His Pro His Ala Val Leu
            340                 345                 350

Thr Pro Leu Asn Ile Val Trp Ala Gly Ile Glu
        355                 360

<210> SEQ ID NO 10
<211> LENGTH: 1092
<212> TYPE: DNA
<213> ORGANISM: Artificial Sequence
<220> FEATURE:
<223> OTHER INFORMATION: mutant protein R166Q nucleotide sequence

<400> SEQUENCE: 10

| | | |
|---|---|---|
| atgaaacaaa caataagcaa tccggcattt gatatgaaac aaattaacgc tcttaacggc | 60 |
| cattatcaga cgatgataga caatggagat ctgcaatgtg cgagttatat gatgtcaaga | 120 |
| ggaggtgagg tttttgcagc tgagtcgtta ggggaattta ccggcggaca aaaagaaaag | 180 |
| caaacatttc agcttgatac aatcagagaa atcggttctt tgacaaaagt gtttaccgct | 240 |
| gtagccgtca tgcagctcgt cgaaaaaggt ttgctcgatc tgaaaatgcc ggtcaagctc | 300 |
| attttgccag cgtttgataa accgggtttc ggagaaatta aaattttgca ccttttgact | 360 |
| catacggcgg gattaagttt tgagctggat attcaaaagg ctgaaggcat tgacttaacg | 420 |
| aatgaggaag aatggataaa ctatctggtc agtacgcctt ggagtacgg agtggatgaa | 480 |
| gcatggaact attcccagac cggctttgtt atacttggca tcattatttc aaaagtaaca | 540 |
| ggcgtatcct acgaacagta tgtaacaaag catattattg aagcgctcgg attagaaaga | 600 |
| acgtattttt atgtgcctga tactttaaaa gaagaagttt gtgtgatcag tgagcacgag | 660 |
| tgcgtacagc tggaaaaaag tcatcacccg tattttccga ataaagcgac aagcggtctg | 720 |
| tactcttcgt tgcgagatat ttggaagtta gctgaaatgt ttagaaataa aggcagattg | 780 |
| aaagataaga agctgcttgg aagaaaaaca gtcgaagcga tgctgagaaa tcaaataaag | 840 |
| cccggtcttc cttttactt cttcggagcg cccagagagg aaggcggctt tggtttaggc | 900 |
| attaatttgt ggccggccgg tgaccattat ttcatgacag aaggcacctt ctcacatctt | 960 |
| ggaatgggtt ggtgcggcat gttttctgat ccagccgaag attttacgta tgtatttttc | 1020 |
| actccgattt ccgagtttca tcctcatgcc gtgctgacgc cgctgaatat cgtgtgggcg | 1080 |
| ggtattgaat aa | 1092 |

<210> SEQ ID NO 11
<211> LENGTH: 362
<212> TYPE: PRT
<213> ORGANISM: Artificial Sequence
<220> FEATURE:
<223> OTHER INFORMATION: mutant protein E128A amino acid sequence

<400> SEQUENCE: 11

```
Met Lys Gln Thr Ile Ser Asn Pro Ala Phe Asp Met Lys Gln Ile Asn
 1               5                  10                  15

Ala Leu Asn Gly His Tyr Gln Thr Met Ile Asp Asn Gly Asp Leu Gln
             20                  25                  30

Cys Ala Ser Tyr Met Met Ser Arg Gly Gly Glu Val Phe Ala Ala Glu
         35                  40                  45

Ser Leu Gly Glu Phe Thr Gly Gly Gln Lys Glu Lys Gln Thr Phe Gln
     50                  55                  60

Leu Asp Thr Ile Arg Glu Ile Gly Ser Leu Thr Lys Val Phe Thr Ala
 65                  70                  75                  80

Val Ala Val Met Gln Leu Val Glu Lys Gly Leu Leu Asp Leu Lys Met
                 85                  90                  95

Pro Val Lys Leu Ile Leu Pro Ala Phe Asp Lys Pro Gly Phe Gly Glu
            100                 105                 110

Ile Lys Ile Leu His Leu Leu Thr His Thr Ala Gly Leu Ser Phe Ala
        115                 120                 125

Leu Asp Ile Gln Lys Ala Glu Gly Ile Asp Leu Thr Asn Glu Glu Glu
    130                 135                 140
```

Trp Ile Asn Tyr Leu Val Ser Thr Pro Leu Glu Tyr Gly Val Asp Glu
145                 150                 155                 160

Ala Trp Asn Tyr Ser Arg Thr Gly Phe Val Ile Leu Gly Ile Ile Ile
            165                 170                 175

Ser Lys Val Thr Gly Val Ser Tyr Glu Gln Tyr Val Thr Lys His Ile
        180                 185                 190

Ile Glu Ala Leu Gly Leu Glu Arg Thr Tyr Phe Tyr Val Pro Asp Thr
    195                 200                 205

Leu Lys Glu Glu Val Cys Val Ile Ser Glu His Glu Cys Val Gln Leu
210                 215                 220

Glu Lys Ser His His Pro Tyr Phe Pro Asn Lys Ala Thr Ser Gly Leu
225                 230                 235                 240

Tyr Ser Ser Leu Arg Asp Ile Trp Lys Leu Ala Glu Met Phe Arg Asn
                245                 250                 255

Lys Gly Arg Leu Lys Asp Lys Lys Leu Leu Gly Arg Lys Thr Val Glu
            260                 265                 270

Ala Met Leu Arg Asn Gln Ile Lys Pro Gly Leu Pro Phe Tyr Phe Phe
        275                 280                 285

Gly Ala Pro Arg Glu Gly Gly Phe Gly Leu Gly Ile Asn Leu Trp
    290                 295                 300

Pro Ala Gly Asp His Tyr Phe Met Thr Glu Gly Thr Phe Ser His Leu
305                 310                 315                 320

Gly Met Gly Trp Cys Gly Met Phe Ser Asp Pro Ala Glu Asp Phe Thr
                325                 330                 335

Tyr Val Phe Phe Thr Pro Ile Ser Glu Phe His Pro His Ala Val Leu
            340                 345                 350

Thr Pro Leu Asn Ile Val Trp Ala Gly Ile
        355                 360

<210> SEQ ID NO 12
<211> LENGTH: 1092
<212> TYPE: DNA
<213> ORGANISM: Artificial Sequence
<220> FEATURE:
<223> OTHER INFORMATION: mutant protein E128A nucleotide sequence

<400> SEQUENCE: 12

```
atgaaacaaa caataagcaa tccggcattt gatatgaaac aaattaacgc tcttaacggc      60
cattatcaga cgatgataga caatggagat ctgcaatgtg cgagttatat gatgtcaaga     120
ggaggtgagg tttttgcagc tgagtcgtta ggggaattta ccggcggaca aaagaaaaag     180
caaacatttc agcttgatac aatcagagaa atcggttctt tgacaaaagt gtttaccgct     240
gtagccgtca tgcagctcgt cgaaaaaggt ttgctcgatc tgaaaatgcc ggtcaagctc     300
attttgccag cgtttgataa accgggtttc ggagaaatta aaattttgca ccttttgact     360
catacggcgg gattaagttt tgcactggat attcaaaagg ctgaaggcat tgacttaacg     420
aatgaggaag aatggataaa ctatctggtc agtacgcctt ggagtacgg agtggatgaa      480 gcatggaact attccagaac cggctttgtt atacttggca tcattatttc aaaagtaaca     540
ggcgtatcct acgaacagta tgtaacaaag catattattg aagcgctcgg attagaaaga     600
acgtattttt atgtgcctga tactttaaaa gaagaagttt gtgtgatcag tgagcacgag     660
tgcgtacagc tggaaaaaag tcatcacccg tattttccga taaaagcgac aagcggtctg     720
tactcttcgt tgcgagatat ttggaagtta gctgaaatgt ttagaaataa aggcagattg     780
```

```
aaagataaga agctgcttgg aagaaaaaca gtcgaagcga tgctgagaaa tcaaataaag    840
cccggtcttc cttttactt cttcggagcg cccagagagg aaggcggctt tggtttaggc    900
attaatttgt ggccggccgg tgaccattat ttcatgacag aaggcacctt ctcacatctt    960
ggaatgggtt ggtgcggcat gttttctgat ccagccgaag attttacgta tgtatttttc   1020
actccgattt ccgagtttca tcctcatgcc gtgctgacgc cgctgaatat cgtgtgggcg   1080
ggtattgaat aa                                                       1092
```

<210> SEQ ID NO 13
<211> LENGTH: 363
<212> TYPE: PRT
<213> ORGANISM: Artificial Sequence
<220> FEATURE:
<223> OTHER INFORMATION: mutant protein E128Q amino acid sequence

<400> SEQUENCE: 13

```
Met Lys Gln Thr Ile Ser Asn Pro Ala Phe Asp Met Lys Gln Ile Asn
1               5                   10                  15

Ala Leu Asn Gly His Tyr Gln Thr Met Ile Asp Asn Gly Asp Leu Gln
            20                  25                  30

Cys Ala Ser Tyr Met Met Ser Arg Gly Gly Glu Val Phe Ala Ala Glu
        35                  40                  45

Ser Leu Gly Glu Phe Thr Gly Gly Gln Lys Gly Lys Gln Thr Phe Gln
    50                  55                  60

Leu Asp Thr Ile Arg Glu Ile Gly Ser Leu Thr Lys Val Phe Thr Ala
65                  70                  75                  80

Val Ala Val Met Gln Leu Val Glu Lys Gly Leu Leu Asp Leu Lys Met
                85                  90                  95

Pro Val Lys Leu Ile Leu Pro Ala Phe Asp Lys Pro Gly Phe Gly Glu
            100                 105                 110

Ile Lys Ile Leu His Leu Leu Thr His Thr Ala Gly Leu Ser Phe Gln
        115                 120                 125

Leu Asp Ile Gln Lys Ala Glu Gly Ile Asp Leu Thr Asn Glu Glu Glu
    130                 135                 140

Trp Ile Asn Tyr Leu Val Ser Thr Pro Leu Glu Tyr Gly Val Asp Glu
145                 150                 155                 160

Ala Trp Asn Tyr Ser Arg Thr Gly Phe Val Ile Leu Gly Ile Ile Ile
                165                 170                 175

Ser Lys Val Thr Gly Val Ser Tyr Glu Gln Tyr Val Thr Lys His Ile
            180                 185                 190

Ile Glu Ala Leu Gly Leu Glu Arg Thr Tyr Phe Tyr Val Pro Asp Thr
        195                 200                 205

Leu Lys Glu Glu Val Cys Val Ile Ser Glu His Glu Cys Val Gln Leu
    210                 215                 220

Glu Lys Ser His His Pro Tyr Phe Pro Asn Lys Ala Thr Ser Gly Leu
225                 230                 235                 240

Tyr Ser Ser Leu Arg Asp Ile Trp Lys Leu Ala Glu Met Phe Arg Asn
                245                 250                 255

Lys Gly Arg Leu Lys Asp Lys Lys Leu Leu Gly Arg Lys Thr Val Glu
            260                 265                 270

Ala Met Leu Arg Asn Gln Ile Lys Pro Gly Leu Pro Phe Tyr Phe Phe
        275                 280                 285

Gly Ala Pro Arg Glu Glu Gly Gly Phe Gly Leu Gly Ile Asn Leu Trp
    290                 295                 300
```

```
Pro Ala Gly Asp His Tyr Phe Met Thr Glu Gly Thr Phe Ser His Leu
305                 310                 315                 320

Gly Met Gly Trp Cys Gly Met Phe Ser Asp Pro Ala Glu Asp Phe Thr
            325                 330                 335

Tyr Val Phe Phe Thr Pro Ile Ser Glu Phe His Pro His Ala Val Leu
            340                 345                 350

Thr Pro Leu Asn Ile Val Trp Ala Gly Ile Glu
            355                 360
```

```
<210> SEQ ID NO 14
<211> LENGTH: 1092
<212> TYPE: DNA
<213> ORGANISM: Artificial Sequence
<220> FEATURE:
<223> OTHER INFORMATION: mutant protein E128Q nucleotide sequence

<400> SEQUENCE: 14
atgaaacaaa caataagcaa tccggcattt gatatgaaac aaattaacgc tcttaacggc      60
cattatcaga cgatgataga caatggagat ctgcaatgtg cgagttatat gatgtcaaga    120
ggaggtgagg tttttgcagc tgagtcgtta ggggaattta ccggcggaca aaagaaaag     180 caaacatttc agcttgatac aatcagagaa atcggttctt tgacaaaagt gtttaccgct    240
gtagccgtca tgcagctcgt cgaaaaaggt ttgctcgatc tgaaaatgcc ggtcaagctc    300
attttgccag cgtttgataa accgggtttc ggagaaatta aaattttgca ccttttgact    360
catacggcgg gattaagttt tcagctggat attcaaaagg ctgaaggcat tgacttaacg    420
aatgaggaag aatggataaa ctatctggtc agtacgcctt ggagtacgg agtggatgaa     480 gcatggaact attccagaac cggctttgtt atacttggca tcattatttc aaaagtaaca    540
ggcgtatcct acgaacagta tgtaacaaag catattattg aagcgctcgg attagaaaga    600
acgtattttt atgtgcctga tactttaaaa gaagaagttt gtgtgatcag tgagcacgag    660
tgcgtacagc tggaaaaaag tcatcacccg tattttccga ataaagcgac aagcggtctg    720
tactcttcgt tgcgagatat ttggaagtta gctgaaatgt ttagaaataa aggcagattg    780
aaagataaga agctgcttgg aagaaaaaca gtcgaagcga tgctgagaaa tcaaataaag    840
cccggtcttc cttttactt cttcggagcg cccagagagg aaggcggctt tggtttaggc    900
attaatttgt ggccggccgg tgaccattat ttcatgacag aaggcacctt ctcacatctt    960 ggaatggggtt ggtgcggcat gttttctgat ccagccgaag attttacgta tgtatttttc   1020
actccgattt ccgagtttca tcctcatgcc gtgctgacgc cgctgaatat cgtgtgggcg   1080
ggtattgaat aa                                                        1092
```

ENZYME WITH ACYL TRANSFER FUNCTION AND APPLICATION THEREOF

CROSS REFERENCE OF RELATED APPLICATION

The present invention claims priority under 35 U.S.C. 119(a-d) to CN 2020100838194, filed Feb. 10, 2020.

BACKGROUND OF THE PRESENT INVENTION

Field of Invention

The present invention relates to a technical field of genetic engineering and biopharmaceuticals, and more particularly to an enzyme with acyl transfer function and application thereof.

Description of Related Arts

The acylation of drugs can usually change the physical and chemical properties and improve the biological efficacy. In drug synthesis, acylation reactions are often used to protect hydroxyl and amino groups; and acyl groups can be converted into other groups through oxidation, reduction, addition, and rearrangement reactions. Therefore, acyltransferase, as a tool enzyme, has become a research hotspot.

Macrolactins refer to a series of 24-membered macrolide compounds, which have biological and pharmacological activities such as antibacterial, antiviral, antitumor, anti-infection and anti-aging. At an earliest stage, the Fenical research group isolated Macrolactins A-F from a strain of deep-sea bacteria in 1989. Studies have shown that Macrolactin A can inhibit B1-F10 murine melanoma cells and mammalian herpes simplex virus, and can protect lymphocytes through inhibiting HIV virus. Through the years, the Macrolactin family has continued to grow. Scientists have successively isolated 7-O-succinyl Macrolactin F, 7-O-succinyl Macrolactin A, Macrolactin G-M (wherein H refers to a 22-membered macrolide and L refers to a bicyclic lactone), Macrolactin N, 7-O-malonyl Macrolactin A, Macrolactin O—R, Macrolactin S and Macrolactin T. These Macrolactins all have good antibacterial activities, wherein Macrolactin N—R can inhibit the peptide deformylase of *Staphylococcus aureus*; 7-O-malonyl Macrolactin A can sufficiently inhibit many gram-positive pathogens such as methicillin-resistant *Staphylococcus aureus*, vancomycin-resistant Enterococci, and *Burkholderia cepacia* varieties; Macrolactins B and T not only inhibit *Staphylococcus aureus*, but also have obvious effects on plant pathogenic fungi Pyricularia *oryzae* and *Alternaria alternata*.

As a class of drug lead compounds with great application potential, Macrolactins have attracted great attention. Macrolactins belong to polyketides, and the skeleton structure Macrolactin A is catalyzed and assembled by polyketide synthases (PKSs). However, the study of subsequent modification steps has not been reported. While studying the post-modification molecular mechanism of Macrolactins, the applicant discovered an enzyme gene that acylated the Macrolactins. Through the acylation reaction of Macrolactins, the pharmacological activity of macrolide compounds can be improved, thereby improving their bioavailability, enhancing drug efficacy, and reducing toxic as well as side effects, which provides a new strategy for the drug development of macrolide compounds.

SUMMARY OF THE PRESENT INVENTION

An object of the present invention is to provide an enzyme with acyl transfer function and its application, which is capable of acylation modification for Macrolactins macrolide compounds, thereby making up for the deficiencies of the prior art.

Accordingly, the present invention provides an acyltransferase, comprising:
a) a protease having a sequence identical to a SEQ ID NO:1;
b) a protease obtained by deleting, substituting, inserting or adding one or several amino acids to the protease in a), which has an acyltransferase activity of the protease in a).

The protein substituting in b) is realized by substitute R at position 166 with A, G, K or Q.

The protein substituting in b) is realized by substitute E at position 128 with A or Q.

A nucleotide sequence of a gene encoding the above acyltransferase is identical to a SEQ ID NO:2.

The present invention also provides a recombinant vector carrying a gene for expressing the acyltransferase of the present invention.

The present invention also provides a transformant prepared by transforming the recombinant vector for expressing the acyltransferase of the present invention into a host cell.

The present invention also provides an application of the above acyltransferase, which binds an acyl group of an acyl donor to a macrolide compound.

The acyl donor is (d)X-CoA, and X represents the acyl group.

The X is selected from a group consisting of acetyl, butyryl, malonyl, succinyl, glutaryl, adipoyl, pimeloyl, suberyl, azelayl and sebacyl.

According to embodiments of the present invention, the macrolide compound is Macrolactins.

The enzyme with the acyl transfer function of the present invention can improve water solubility of the macrolide compounds through acylation reaction of the Macrolactins, thereby improving bioavailability, enhancing efficacy, and reducing toxic as well as side effects, which provides a new strategy for the drug development of macrolide compounds.

DETAILED DESCRIPTION OF THE PREFERRED EMBODIMENT

Figure 1:
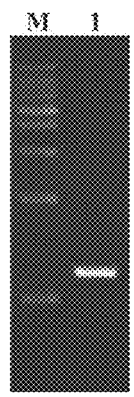
FIG. 1 is an electrophoresis diagram of an encoded acyltransferase gene bmmI amplified by the present invention.

First, terms involved in the present invention will be explained as follows.

"Multiple amino acids" refers to 2 to 5 amino acids, and preferably 2 to 3 amino acids. The deletion, addition, insertion or substitution of one or more amino acids to the amino acid sequence of related sequence number can be modified by conventional techniques such as site-directed mutagenesis to modify the DNA sequence encoding the protein containing the amino acid sequence of each sequence number. Preferably, substitution of amino acid residue is a conservative substitution. It is known that conservative substitutions can occur between the following amino acid residues: glycine (Gly) and proline (Pro), glycine and alanine (Ala) or valine (Val), leucine (Leu) and iso Leucine (Ile), Glutamate (Glu) and Glutamine (Gln), Aspartate (Asp) and Asparagine (Asn), Cysteine (Cys) and Threonine (Thr), Threonine and Serine (Ser) or Alanine, as well as Lysine (Lys) and Arginine (Arg).

Acyltransferase gene: the acyltransferase gene of the present invention is a gene encoding a protein having an activity which transfers an acyl group from the above-mentioned acyltransferase (i.e., an acyl donor) to an arbitrary compound (i.e., acylation of an arbitrary compound). Specifically, the acyltransferase gene of the present invention comprises DNA encoding the above-mentioned acyltransferase.

The acyltransferase gene of the present invention comprises a gene functionally equivalent to a gene containing DNA having a nucleotide sequence identical to a SEQ ID NO: 2. The "functionally equivalent gene" means that the protein encoded by the gene has biological and biochemical functions equivalent to those of the protein encoded by the acyltransferase gene of the present invention. An example of the methods known to those skilled in the art for preparing a gene functionally equivalent to a specific gene is hybridization technology. Therefore, the acyltransferase gene of the present invention comprises a gene that hybridizes with DNA containing a nucleotide sequence complementary to the nucleotide sequence SEQ ID NO: 2 under stringent conditions and encodes a protein having acyltransferase activity.

The term "stringent conditions" refers to conditions under which specific heterozygotes are formed, but non-specific heterozygotes are not formed. These conditions comprise low stringency conditions and high stringency conditions, and high stringency conditions are preferred. The low stringency conditions comprise washing with 5×SSC and 0.1% SDS at 42° C. after hybridization, and preferably washing with 5×SSC and 0.1% SDS at 50° C. The high stringency conditions comprise washing with 0.1×SSC and 0.1% SDS at 65° C. after hybridization. The DNA, whose nucleotide sequence is highly homologous with the nucleotide sequence of the SEQ ID NO: 2 (ie, having 80% or greater, preferably 90% or greater, more preferably 95% or greater, and further preferably 98% or greater homology; or having 80% or greater, preferably 90% or greater, more preferably 95% or greater, and further preferably 98% or greater identity), can hybridize with DNA containing a nucleotide sequence complementary to the nucleotide sequence of the DNA under the above stringent conditions.

Furthermore, the present invention relates to a recombinant vector containing the above-mentioned acyltransferase gene. The recombinant vector of the present invention can be constructed by introducing the above-mentioned acyltransferase gene into a suitable vector. The type of the vector is not particularly limited, which can be pBI, pPZP, pSMA, pUC, pBR, pBluescript, pET, pGEM, pKS1 and pTriEX™ vectors (TAKARA); and pTrcHis2-TOPO vector (Invitrogen). In addition, viral vectors such as cauliflower mosaic virus (CaMV), bean golden mosaic virus (BGMV), and tobacco mosaic virus (TMV) can be used. Alternatively, pBI binary vector can be used.

In order to insert the gene into the vector, the DNA to be inserted can be cut with a suitable restriction endonuclease, and then the DNA fragment is inserted at the restriction endonuclease site or multiple cloning site of the suitable vector DNA to connect to the vector DNA.

It is necessary to integrate the above-mentioned gene into the vector while allowing the gene to function in it. For this purpose, the vector may contain elements such as promoters, introns, enhancers, translation stop codons, terminators, polyadenylic acid addition signals, and 5'-untranslated region sequences within, at upstream or downstream of the gene. In addition, the vector may contain a selectable marker gene. Conventionally vector elements can be used in combination in a suitable manner.

Promoters that can function in bacterial cells comprise: raw maltoyl amylase gene promoter of *Bacillus stearothermophilus*, α amylase gene promoter of *Bacillus licheniformis*, BAN amylase gene promoter of *Bacillus amyloliquefaciens*, alkaline protease gene promoter of *Bacillus subtilis*, xylosidase gene promoter of *Bacillus pumilus*, PR or PL promoter of phage, and lac, trp or tac promoter of *Escherichia coli*.

Promoters that can function in yeast host cells comprise promoters derived from genes of yeast acyl glycolysis system, alcohol dehydrogenase gene promoters, TPI1 promoters, and ADH2-4c promoters. Promoters that can function in fungi comprise ADH3 promoter and tipA promoter.

The terminators comprise nopaline synthase (NOS) gene terminator, octopine synthase (OCS) gene terminator, CaMV 35S terminator, *E. coli* lipoprotein lpp 3' terminator, trp operon terminator, amyB terminator, and ADH1 gene terminator. The translation stop codons comprises sequences such as TAA, TAG or TGA.

The present invention also relates to transformants produced by introducing a recombinant vector containing the above-mentioned acyltransferase gene into a suitable host.

The host is not restricted as long as the introduced gene can be expressed therein. The host may be bacteria such as *Escherichia coli* and *Bacillus subtilis*, yeasts such as *Saccharomyces cerevisiae, Schizosaccharomyces pombe* and *Pichia pastoris*, and filamentous fungi such as *Aspergillus, Neurospora, Fusarium* and *Trichoderma*.

The present invention also provides mutant proteins (R166A, R166G, R166K, R166Q, E128A and E128Q) constructed by site-directed mutagenesis, which can greatly broaden the selectivity of acyl donors and improve the catalytic efficiency. Compared with the wild-type protein, R166A, R166G and R166Q mutant proteins can select acyl donors with side chain lengths of C3-C12. The catalytic efficiency of E128A and E128Q towards malonyl-CoA, succinyl-CoA and glutaryl-CoA is 1.5-2 times higher than that of the wild type.

The present invention also provides applications of the above acyltransferase, which binds an acyl group of an acyl donor to a macrolide compound;

The acyl donor is (d)X-CoA, and X represents the acyl group.

The X is selected from a group consisting of acetyl, butyryl, malonyl, succinyl, glutaryl, adipoyl, pimeloyl, suberyl, azelayl and sebacyl.

The acyltransferase of the present invention is suitable for acylating macrolide compounds, preferably Macrolactins.

The present invention will be further described below in conjunction with specific embodiments.

Embodiment 1: Cloning of Acyltransferase Gene

1. Extraction of Genomic DNA

Inoculating marine-derived *Bacillus* methylotrophicus B-9987 in 10 mL LB liquid medium, culturing overnight at 37° C., collecting the bacteria by centrifugation, and discarding the supernatant; washing twice with 1 mL of STE buffer; adding 500 µL of STE buffer to prepare 3-5 mg/mL lysozyme solution, carefully and fully suspending the bacteria, processing in a 37° C. water bath for 30 min, until the cells become translucent; adding 250 µL of 3% SDS, gently shaking up and down, continuing to 37° C. water bath until clear; add 1/10 volume of 3 M NaAc (pH=4.8), and then adding 200 µL of phenol:chloroform:isoamyl alcohol (25:24:1), inverting the centrifuge tube several times, and centrifuging at 12,000 rpm for 10 min; carefully pipetting the supernatant and repeatedly extract with phenol:chloroform:isoamyl alcohol until the middle layer is free of protein impurities, transferring the supernatant, adding an equal volume of isopropanol (or 2 times the volume of absolute ethanol), mix upside down until white flocculent DNA precipitates; picking out the flocculent precipitate and washing with 70% ethanol for 1-2 times; after drying at room temperature, dissolving genomic DNA (T-DNA) with 100 µL of TE; adding 400 µL of TE to DNA, adding 10 µL of 5 mg/mL RNase, incubating at 37° C. for 30 min to remove the RNA; adding 100 µL of 6% SDS, 6 µL of 0.5 M EDTA and 4 µL of 10 mg/mL proteinase K, mixing and reacting at 37° C.-55° C. for more than 1 hour; adding 200 µL of Tris balance phenol:chloroform:isoamyl alcohol (25:24:1) to extract until the middle contains no protein layer; adding 2 times absolute ethanol to re-precipitate T-DNA, picking out flocculent DNA into 70% ethanol, washing 1-2 times, and centrifuging to precipitate DNA; drying at room temperature and dissolving in 100 µL TE for later use.

2. Cloning of bmmI Acyltransferase Gene

Designing primer pair: P1: 5'-ATGAAACAAACAATAAGC-3'/P2: 5'-TTCAATACCCGCC-CACACG-3', diluting the T-DNA of marine-derived *Bacillus* methylotrophicus B-9987 prepared above by 5 times as a template for PCR. A reaction system (100 µL) is as follows: primers P1 and P2 each 5 µL (50 pmol), template 5 µL, 10× Reaction Buffer 10 µL, 2.5 mM dNTP 10 µL, 25 mM MgCl$_2$ 6 µL, Taq DNA Polymerase 1 µL (5 U/µL) (TaKaRa), adding ddH$_2$O to 100 µL.

PCR conditions are: denaturation at 94° C. for 4 min; 94° C. for 40 s, 51° C. for 40 s, 72° C. for 1 min, 30 cycles; 72° C. for 8 min. FIG. 1 illustrates the electrophoresis results. The gene was cloned into the pUM-T vector, and transformed into *E. coli* DH5a competent cells. Positive clones were selected and sent to Shanghai Sunny Biotechnology Company for sequence determination. The results are shown in SEQ ID NO: 2, and a translated protease sequence is SEQ ID NO:1. The results of multiple sequencing proved the correctness of the sequence.

The nucleotide sequence of the gene is as follows (SEQ ID NO: 2):

ATGAAACAAACAATAAGCAATCCGGCATTTGATATGAAACAAATTAACG

CTCTTAACGGCCATTATCAGACGATGATAGACAATGGAGATCTGCAATG

TGCGAGTTATATGATGTCAAGAGGAGGTGAGGTTTTTGCAGCTGAGTCG

TTAGGGGAATTTACCGGCGGACAAAAAGAAAAGCAAACATTTCAGCTTG

ATACAATCAGAGAAATCGGTTCTTTGACAAAAGTGTTTACCGCTGTAGC

CGTCATGCAGCTCGTCGAAAAAGGTTTGCTCGATCTGAAAATGCCGGTC

AAGCTCATTTTGCCAGCGTTTGATAAACCGGGTTTCGGAGAAATTAAAA

TTTTGCACCTTTTGACTCATACGGCGGGATTAAGTTTTGAGCTGGATAT

TCAAAAGGCTGAAGGCATTGACTTAACGAATGAGGAAGAATGGATAAAC

TATCTGGTCAGTACGCCTTTGGAGTACGGAGTGGATGAAGCATGGAACT

ATTCCAGAACCGGCTTTGTTATACTTGGCATCATTATTTCAAAAGTAAC

AGGCGTATCCTACGAACAGTATGTAACAAAGCATATTATTGAAGCGCTC

GGATTAGAAAGAACGTATTTTTATGTGCCTGATACTTTAAAAGAAGAAG

TTTGTGTGATCAGTGAGCACGAGTGCGTACAGCTGGAAAAAAGTCATCA

CCCGTATTTTCCGAATAAAGCGACAAGCGGTCTGTACTCTTCGTTGCGA

GATATTTGGAAGTTAGCTGAAATGTTTAGAAATAAAGGCAGATTGAAAG

ATAAGAAGCTGCTTGGAAGAAAAACAGTCGAAGCGATGCTGAGAAATCA

AATAAAGCCCGGTCTTCCTTTTTACTTCTTCGGAGCGCCCAGAGAGGAA

GGCGGCTTTGGTTTAGGCATTAATTTGTGGCCGGCCGGTGACCATTATT

TCATGACAGAAGGCACCTTCTCACATCTTGGAATGGGTTGGTGCGGCAT

GTTTTCTGATCCAGCCGAAGATTTTACGTATGTATTTTTCACTCCGATT

TCCGAGTTTCATCCTCATGCCGTGCTGACGCCGCTGAATATCGTGTGGG

CGGGTATTGAATAA

The protease sequence is as follows (SEQ ID NO: 1):

MKQTISNPAFDMKQINALNGHYQTMIDNGDLQCASYMMSRGGEVFAAES

LGEFTGGQKEKQTFQLDTIREIGSLTKVFTAVAVMQLVEKGLLDLKMPV

KLILPAFDKPGFGEIKILHLLTHTAGLSFELDIQKAEGIDLTNEEEWIN

-continued

```
YLVSTPLEYGVDEAWNYSRTGFVILGIIISKVTGVSYEQYVTKHIIEAL

GLERTYFYVPDTLKEEVCVISEHECVQLEKSHHPYFPNKATSGLYSSLR

DIWKLAEMFRNKGRLKDKKLLGRKTVEAMLRNQIKPGLPFYFFGAPREE

GGFGLGINLWPAGDHYFMTEGTFSHLGMGWCGMFSDPAEDFTYVFFTPI

SEFHPHAVLTPLNIVWAGIE
```

3. Expression of bmmI Gene in *E. coli* Cells

Figure 2:
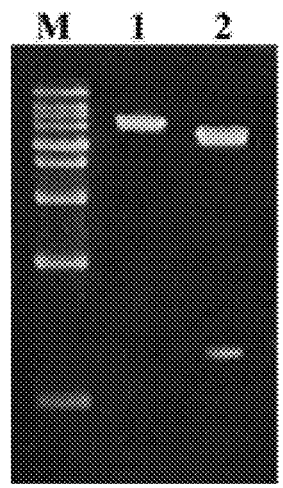
FIG. 2 is a construction verification electrophoresis diagram of an expression vector constructed in the embodiment 3 of the present invention, wherein M: 1 kb DNA molecular weight marker; lane 1: pET28a/bmmI digested with NdeI; lane 2: pET28a/bmmI digested with NdeI and XhoII.
Figure 3:
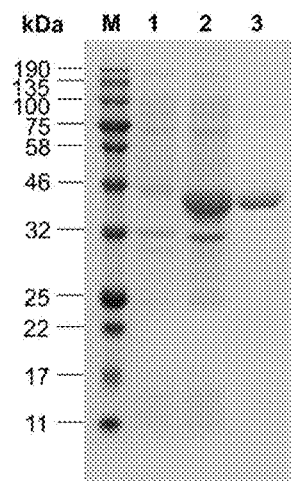
FIG. 3 is an SDS-PAGE analysis electrophoresis diagram of a purified acyltransferase BmmI, wherein M: protein marker; lane 1: supernatant of *E. coli* Rosetta (DE3)/pET28a; lane 2: supernatant of *E. coli* Rosetta (DE3)/pET28a/bmmI; lane 3: purified N. C-(His)6-tagged recombinant protein BmmI with a calculated molecular weight of 40.9 KDa.

In order to express the BmmI protein, using the cloned full-length bmmI gene as a template, and using primers containing NdeI and XhoI restriction sites (P3: 5'-GGGAAT-TC<u>CATATG</u>AAACAAACAATAAGC-3'/P4: 5'-CCG<u>CTCGAG</u>TTCAATACCCGCCCACACG-3', the underlined parts are NdeI and XhoI restriction sites), amplifying the open reading frame of the bmmI gene by PCR. Digesting the amplified DNA fragments with two restriction enzymes, NdeI and XhoI, and cloning them into plasmid pET-28a to construct recombinant plasmid pET-28a-bmmI. After construction, performing restriction enzyme digestion and PCR identification, wherein the results are shown in FIG. 2. Then introducing into *E. coli* Rosetta (DE3) cells, and inducing the target protein to express with isopropyl thiogalactoyl glycoside (IPTG). Disrupting the bacteria by ultrasound, and performing affinity purification by Ni column and concentration by ultrafiltration, so as to obtain an enzyme extract with high purity, wherein the molecular weight and purity of the target protein were tested by sodium dodecyl sulfate polyacrylamide gel electrophoresis (SDS-PAGE); the results are shown in FIG. 3; the concentration of the enzyme extract was determined by the Bradford method. Adding glycerin which is 50% of the total volume of the enzyme extract and DTT with a final molar concentration of 0.01 mmol/L into the obtained enzyme extract. Storing at −20° C. for later use. Avoiding repeated freezing and thawing to prevent the enzyme activity from decreasing.

Embodiment 2: In Vitro Enzyme Activity Detection of BmmI Protein

In vitro enzyme activity reaction system: (100 µL)
1 M Tris-HCl buffer (pH8.5): 1.5 µL
0.5 M $MgCl_2$: 0.12 µL
500 µM Macrolactin A: 3 µL
10 mM Succinyl-CoA: 1.5 µL
37.54 mM BmmI protein: 0.8 µL
$ddH_2O$: 23.08 µL Reaction conditions: 30° C., 2 h. After the reaction is over, adding 30 µL of acetonitrile to stop the reaction, centrifuging at 13,000 rpm for 20 min, discarding the precipitate, and removing the protein in the reaction solution. The obtained supernatant was tested by HPLC.

HPLC detection: using reverse phase C18 column (specification: 150×4.6 mm, 5 µm) with a column temperature of 30° C.; elution conditions: 0-5 min equilibrium: 55% phase A ($ddH_2O$+0.1% formic acid) and 45% phase B (acetonitrile+0.1% formic acid); 5-15 min linear elution: 55-30% phase A and 45-70% phase B; 15-25 min isocratic elution: 0% phase A and 100% phase B; wherein detection wavelength is 260 nm, and flow rate is 1 mL/min. From the spectrum obtained by HPLC (FIG. 4A), a new absorption peak consistent with the UV absorption spectrum of the substrate appeared after the reaction (FIG. 5A, Macrolactins UV absorption spectrum), indicating the occurrence of the enzymatic reaction.

Figure 6:
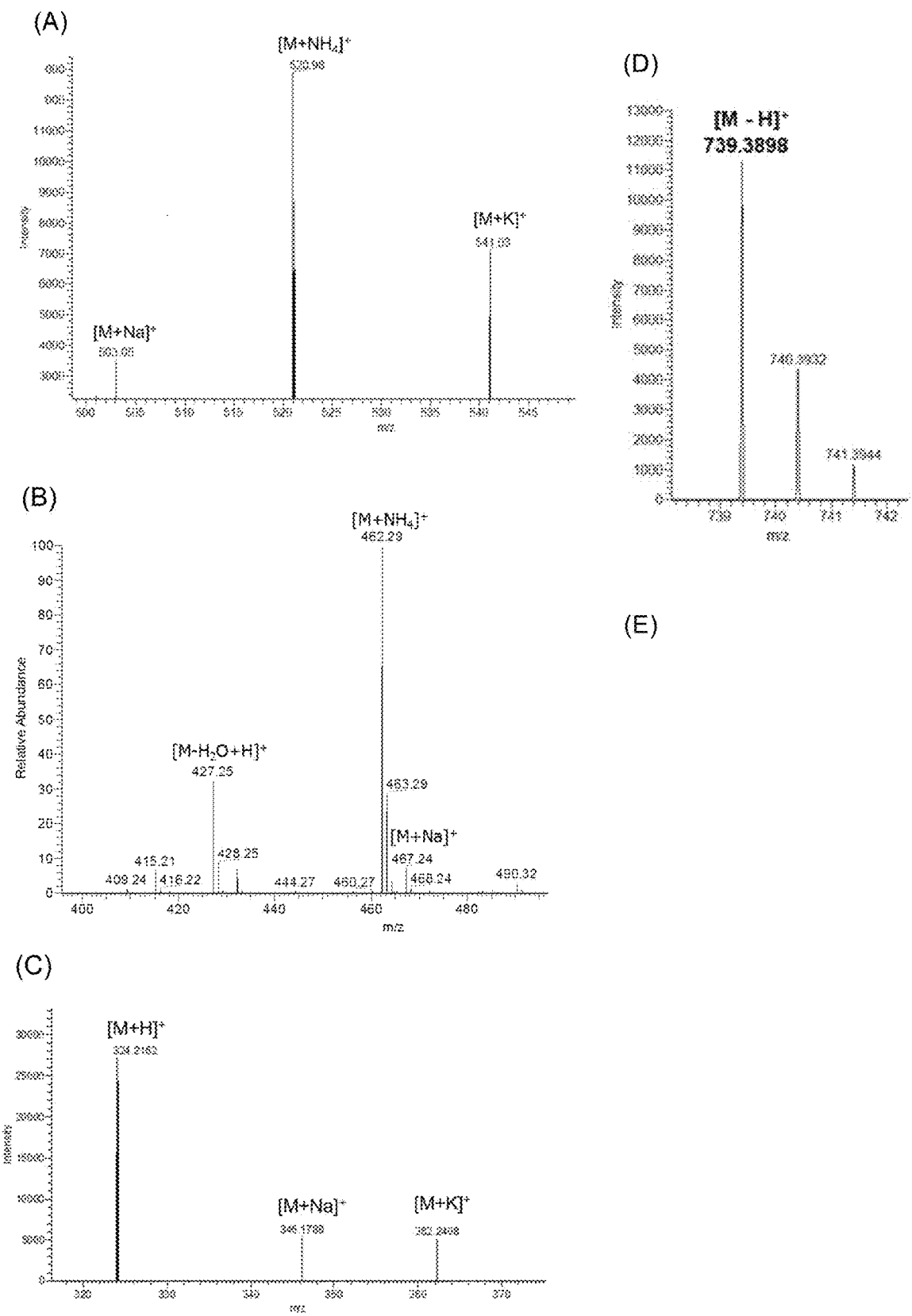
FIG. 6 is mass spectra of acylation products, wherein (A) is a mass spectrum of succinylated Macrolactin A; (B) is a mass spectrum of acetylated Macrolactin A; (C) is a mass spectrum of succinylated Chloramphenicol; (D) is a mass spectrum of malonylated Filipin III; (E) is a mass spectrum of malonylated Glycosylated piericidin A.

The obtained solution containing the acylation product was subjected to high resolution mass spectrometry (HRMS) analysis (FIG. 6A). From the MS spectrum, the obtained product $[N+NH_4]^+$ is 520.98, $[M+Na]^+$ is 503.05, wherein the molecular weight is consistent with that of the expected target product. The above results confirmed that succinylated Macrolactin A was prepared in the reaction solution.

Figure 4:
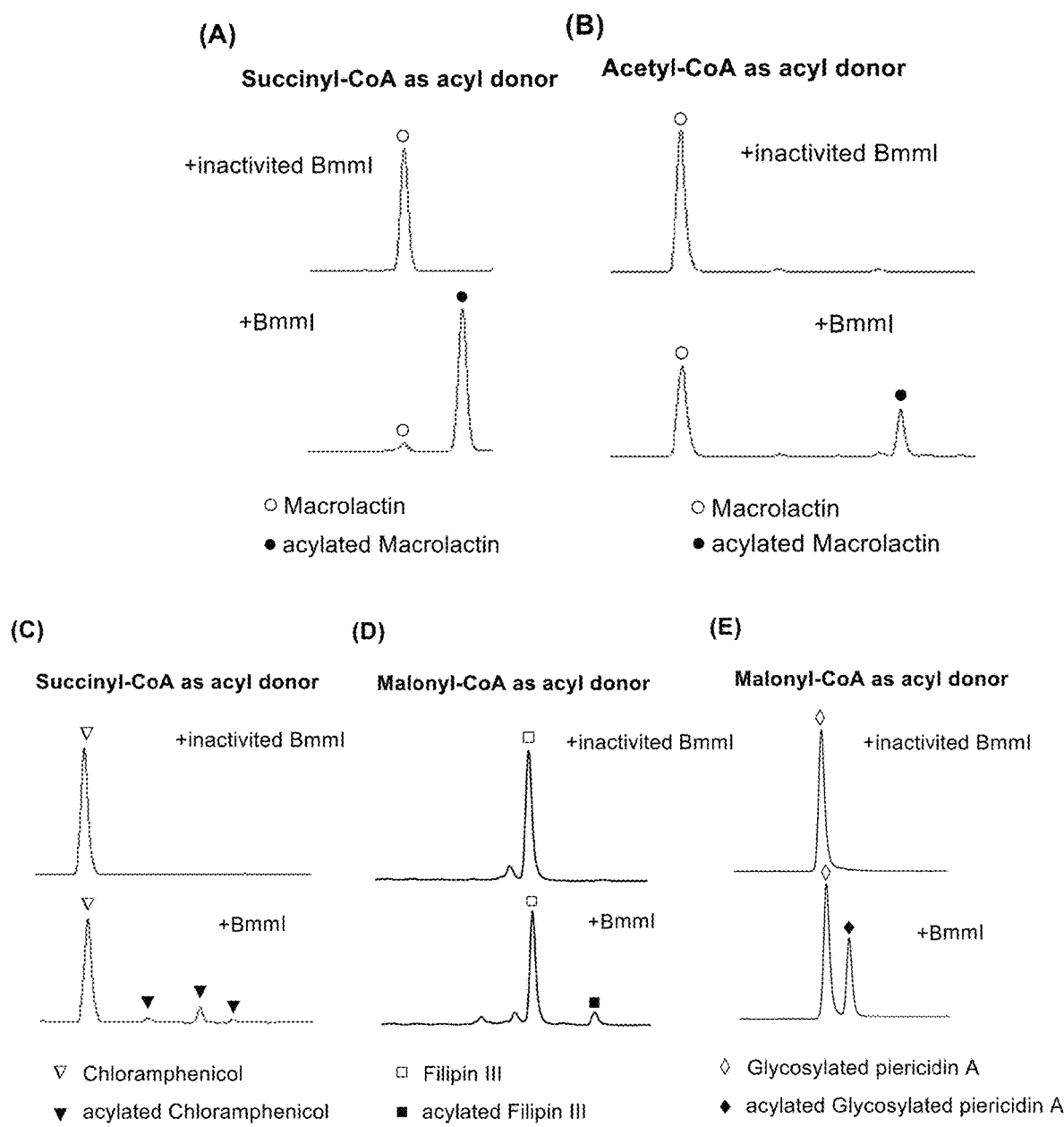
FIG. 4 is high performance liquid chromatography (HPLC) spectra of acylation products, wherein (A) is a high performance liquid chromatography (HPLC) spectrum of succinylated Macrolactin A; (B) is a high performance liquid chromatography (HPLC) spectrum of acetylated Macrolactin A; (C) is a high performance liquid chromatography (HPLC) spectrum of succinylated Chloramphenicol; (D) is a high performance liquid chromatography (HPLC) spectrum of malonylated Filipin III; (E) is a high performance liquid chromatography (HPLC) spectrum of malonylated Glycosylated piericidin A.
Figure 5:
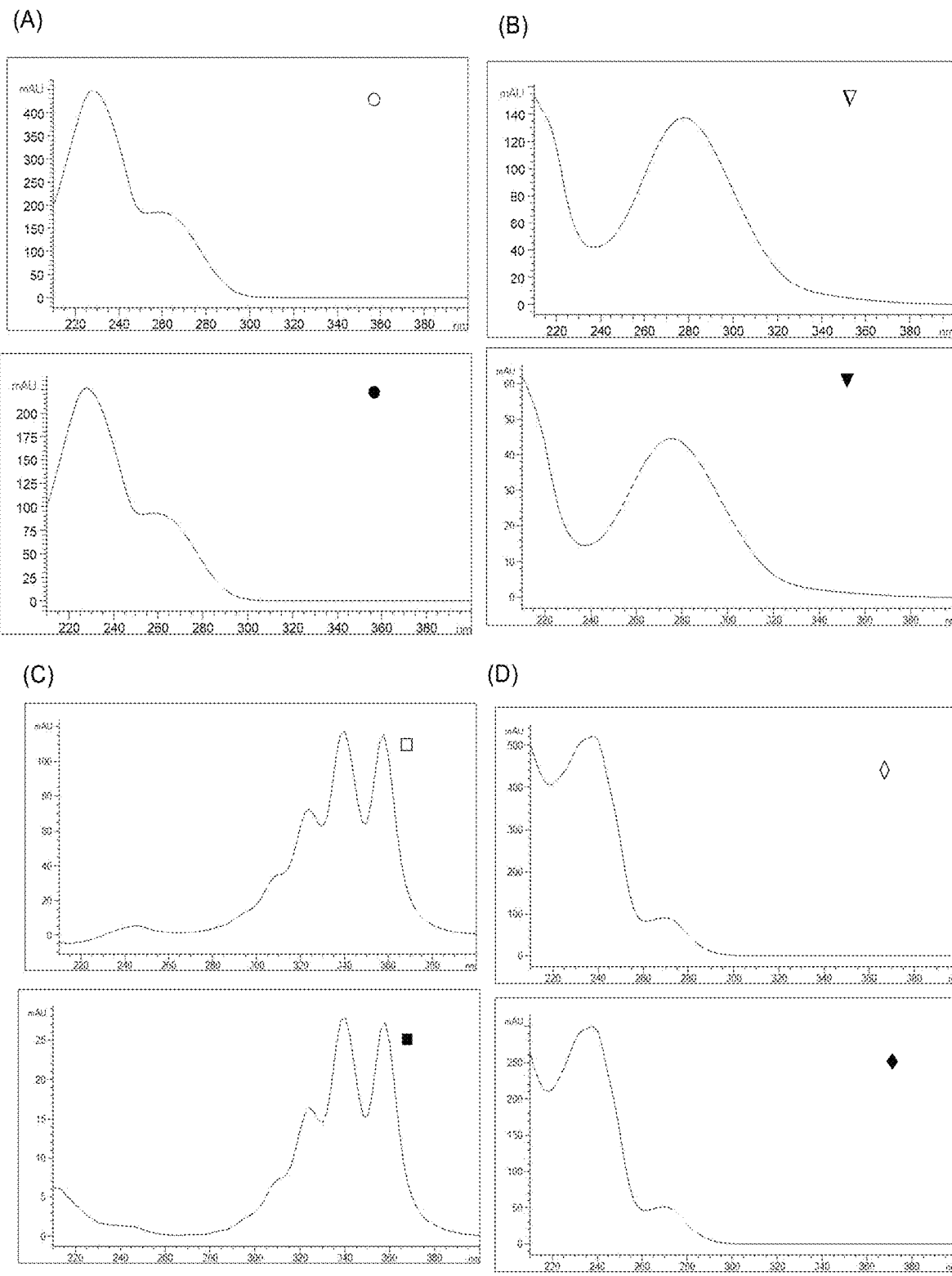
FIG. 5 is UV absorption spectra of Macrolactin A, Chloramphenicol, Filipin III, Glycosylated piericidin A and acylation products, wherein (A) is a UV absorption spectrum of Macrolactin A and acylation products; (B) is a UV absorption spectrum of Chloramphenicol and acylation products; (C) is a UV absorption spectrum of Filipin III and acylation products; (D) is a UV absorption spectrum of Glycosylated piericidin A and acylation products.

Embodiment 3: Transacylation Effect of BmmI Acyltransferase on Macrolide Compounds When Acetyl-CoA is used as the acyl donor, the Succinyl-CoA in the enzyme reaction system as shown in the embodiment 2 is replaced with Acetyl-CoA. After incubating at 30° C. for 2 hours, the reaction is terminated and then HPLC detection and HRMS analysis are performed (FIGS. 4B, 5A, 6B). From the MS spectrum, the obtained product $[M+NH_4]^+$ is 462.29, $[M+Na]^+$ is 467.24, wherein the molecular weight is consistent with that of the expected target product. The above results confirmed that acetylated Macrolactin A was also obtained, which proves that the acyltransferase of the present invention has good application prospects.

Embodiment 4: Transacylation Effect of BmmI Acyltransferase on Chloramphenicol

When Succinyl-CoA is used as the acyl donor, the Macrolactin A in the enzyme reaction system as shown in the embodiment 2 is replaced with Chloramphenicol. After incubating at 30° C. for 2 hours, the reaction is terminated and then HPLC detection and HRMS analysis are performed (FIGS. 4C, 5B, 6C). From the MS spectrum, the obtained product $[M+K]^+$ is 362.2408, $[M+Na]^+$ is 346.1788, wherein the molecular weight is consistent with that of the expected target product. The above results confirmed that acetylated Chloramphenicol was also obtained.

Embodiment 5: Transacylation Effect of BmmI Acyltransferase on Filipin

When Malonyl-CoA is used as the acyl donor, the Macrolactin A in the enzyme reaction system as shown in the embodiment 2 is replaced with Filipin III. After incubating at 30° C. for 2 hours, the reaction is terminated and then HPLC detection and FIRMS analysis are performed (FIGS. 4D, 5C, 6D). From the MS spectrum, the obtained product $[M-H]^+$ is 739.3898, wherein the molecular weight is consistent with that of the expected target product. The above results confirmed that the acylated Filipin III was also obtained.

Embodiment 6: Transacylation Effect of BmmI Acyltransferase on Glycosylated Piericidin When Malonyl-CoA is used as the acyl donor, the Macrolactin A in the enzyme reaction system as shown in the embodiment 2 is replaced with Glycosylated piericidin A. After incubating at 30° C. for 2 hours, the reaction is terminated and then HPLC detection and HRMS analysis are performed (FIGS. 4E, 5D, 6E). From the MS spectrum, the obtained product $[M-H]^+$ is 662.3171, wherein the molecular weight is consistent with that of the expected target product. The above results confirmed that the acylated Glycosylated piericidin A was also obtained.

Embodiment 7: Determination of the Efficiency of BmmI Wild-Type Protein and Mutant Protein in Catalyzing Different Acyl Donors The applicant's research found that by deleting, substituting, inserting or adding one or several amino acids to the enzyme sequence SEQ ID NO:1, the obtained enzyme with new sequence also has the function of acyl transfer. For example, the QI at position 3 and 5 of the protein sequence are replaced by other amino acid residues such as H and L; the TE at positions 67 and 70 are replaced by other amino acid residues such as S and K; the S and E at positions 126 and 128 are replaced by other amino acid residues such as A and D; VIS at positions 215-217 are replaced by other amino acid residues such as IVN; MS at positions 327 and 329 are replaced by other amino acid residues such as LV; H at positions 347 and 349 are replaced by other amino acid residues such as N and E. According to the enzyme activity detection method of the embodiment 2, all of the above-mentioned derived enzymes have the same function as that of the acyltransferase of SEQ ID NO:2.

With Malonyl-CoA, Succinyl-CoA, Glutaryl-CoA, Hexanedioyl-CoA, Heptanedioyl-CoA, Octanedioyl-CoA, Decanedioyl-CoA, Dodecanedioyl-CoA, Acetyl-CoA and Butyryl-CoA as acyl donors, the BmmI protein in the enzyme reaction system of the embodiment 2 is replaced with mutant proteins R166A, R166G, R166K, R166Q, E128A and E128Q (see Table 1 for related information). After incubating at 30° C. for 2 hours, the reaction is terminated and HPLC detection is performed to detect decrement of the substrate Macrolactin A, thereby calculating the reaction efficiency and comparing with the BmmI wild-type protein.

TABLE 1

Sequence information of BmmI mutant proteins

| Mutant Name | Amino acid substitution position | Amino acid substitution | Amino acid sequence | Nucleotide sequence |
| --- | --- | --- | --- | --- |
| R166A | 166 | R→A | SEQ ID NO: 3 | SEQ ID NO: 4 |
| R166G | 166 | R→G | SEQ ID NO: 5 | SEQ ID NO: 6 |
| R166K | 166 | R→K | SEQ ID NO: 7 | SEQ ID NO: 8 |
| R166Q | 166 | R→Q | SEQ ID NO: 9 | SEQ ID NO: 10 |
| E128A | 128 | E→A | SEQ ID NO: 11 | SEQ ID NO: 12 |
| E128Q | 128 | E→Q | SEQ ID NO: 13 | SEQ ID NO: 14 |

Figure 7:
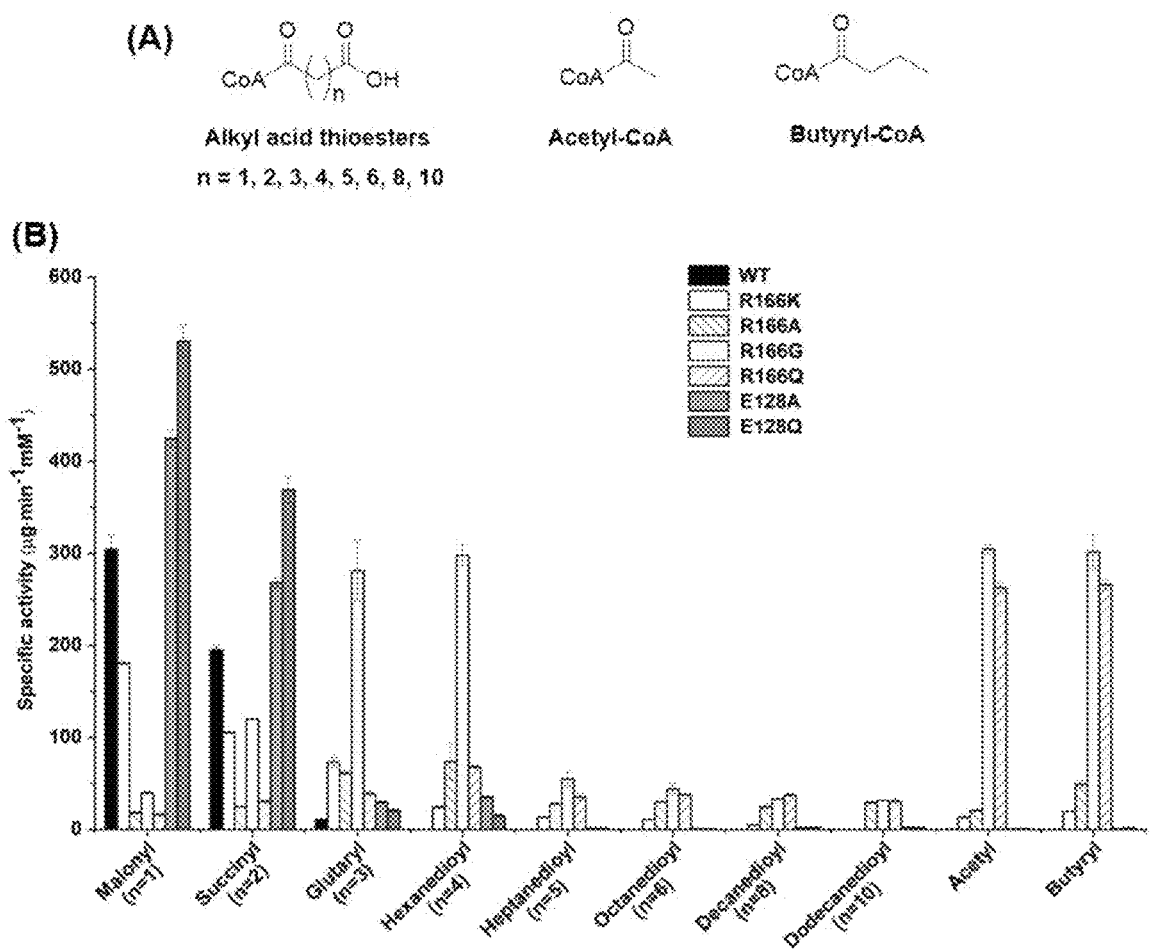
FIG. 7 illustrates catalysis efficiencies of wild-type protein and mutant protein towards different acyl donors.

Referring to FIG. 7, the wild-type BmmI protein can only recognize malonyl-CoA (C3), succinyl-CoA (C4), glutaryl-CoA (C5) and hexanedioyl-CoA (C6) as the acyl donors, while the mutant protein R166A, R166G, R166Q, and R166K can recognize acyl donors with side chain lengths of C3-C12, which greatly broadens the selectivity of acyl donors. Furthermore, the catalytic efficiency of mutant protein R166G towards glutaryl-CoA, hexanedioyl-CoA, acetyl-CoA, and acetyl-CoA is equivalent to that of the wild-type protein towards malonyl-CoA. Compared with the wild-type protein, the catalytic efficiency of the mutant proteins E128A and E128Q towards malonyl-CoA, succinyl-CoA and glutaryl-CoA is increased by 1.5-2 times.

---

What is claimed is:

1. An acyltransferase, comprising:
    a) a protease having a sequence identical to a SEQ ID NO:1;
    b) a protease obtained by substituting R at position 166 or substituting E at position 128 of the protease in a), which has an acyltransferase activity of the protease in a).

2. The acyltransferase, as recited in claim 1, wherein the protein substituting in b) is realized by substituting R at position 166 with A, G, K or Q.

3. The acyltransferase, as recited in claim 1, wherein the protein substituting in b) is realized by substituting E at position 128 with A or Q.

* * * * *